(12) United States Patent
Yuksel

(10) Patent No.: US 9,846,933 B2
(45) Date of Patent: Dec. 19, 2017

(54) SYSTEMS AND METHODS FOR MONITORING COMPONENTS

(71) Applicant: General Electric Company, Schenectady, NY (US)

(72) Inventor: Basak Yuksel, Istanbul (TR)

(73) Assignee: General Electric Company, Schenectady, NY (US)

( * ) Notice: Subject to any disclaimer, the term of this patent is extended or adjusted under 35 U.S.C. 154(b) by 55 days.

(21) Appl. No.: 14/942,039

(22) Filed: Nov. 16, 2015

(65) Prior Publication Data

US 2017/0140515 A1    May 18, 2017

(51) Int. Cl.
| | | |
|---|---|---|
| G06K 9/00 | (2006.01) | |
| G06T 7/00 | (2017.01) | |
| G06T 7/40 | (2017.01) | |

(52) U.S. Cl.
CPC ............ *G06T 7/001* (2013.01); *G06T 7/0002* (2013.01); *G06T 7/0004* (2013.01); *G06T 7/0008* (2013.01); *G06T 7/0085* (2013.01); *G06T 7/407* (2013.01); *G06T 2207/30164* (2013.01)

(58) Field of Classification Search
CPC ......... G06T 11/001; G06T 2207/10148; G06T 2207/10152; G06T 7/0014; G06T 7/001; G06T 7/0085; G06T 2207/30164; G06T 7/0002; G06T 7/0004; G06T 7/0008; G06K 19/0717; G06K 9/00604; G01N 21/84; G01N 33/00; G01N 33/0031; G01N 33/0075; G08B 13/02; G08B 21/18; G08B 29/181

USPC .......................................................... 382/152
See application file for complete search history.

(56) References Cited

U.S. PATENT DOCUMENTS

| | | | |
|---|---|---|---|
| 4,528,856 A | 7/1985 | Junker et al. | |
| 4,746,858 A | 5/1988 | Metala et al. | |
| 4,782,705 A | 11/1988 | Hoffmann et al. | |
| 4,859,062 A | 8/1989 | Thurn et al. | |
| 4,875,170 A | 10/1989 | Sakurai et al. | |
| 6,078,396 A | 6/2000 | Manzouri | |
| 6,175,644 B1 * | 1/2001 | Scola ................. | G01N 21/8851 |
| | | | 117/201 |

(Continued)

FOREIGN PATENT DOCUMENTS

| | | |
|---|---|---|
| EP | 1266262 | 12/2002 |
| WO | WO01/71418 | 9/2001 |

(Continued)

*Primary Examiner* — Kanjibhai Patel
(74) *Attorney, Agent, or Firm* — Dority & Manning, P.A.

(57) ABSTRACT

Systems and methods for monitoring components are provided. A component has an exterior surface. A method includes performing a first analysis of a first image of a surface feature configured on the exterior surface of the component, the first image obtained by an imaging device. The method further includes adjusting a viewing parameter of the imaging device when a predetermined first analysis threshold for the first image is unsatisfied, and performing a subsequent first analysis of a second image of the surface feature, the second image obtained by the imaging device. The method further includes adjusting a distance between the imaging device and the surface feature when the predetermined first analysis threshold for the second image is unsatisfied, and performing a second analysis of a third image, the third image obtained by the imaging device.

28 Claims, 5 Drawing Sheets

(56) References Cited

U.S. PATENT DOCUMENTS

| | | |
|---|---|---|
| 6,574,363 B1 | 6/2003 | Classen et al. |
| 6,983,659 B2 | 1/2006 | Soechting et al. |
| 6,986,287 B1 | 1/2006 | Dorfman |
| 7,200,259 B1 | 4/2007 | Gold et al. |
| 7,227,648 B2 | 6/2007 | Weinhold |
| 7,414,732 B2 | 8/2008 | Maidhof et al. |
| 7,421,370 B2 | 9/2008 | Jain et al. |
| 7,441,464 B2 | 10/2008 | Turnbull et al. |
| 7,477,995 B2 | 1/2009 | Hovis et al. |
| 7,490,522 B2 | 2/2009 | Ruehrig et al. |
| 7,533,818 B2 | 5/2009 | Hovis et al. |
| 7,689,003 B2 | 3/2010 | Shannon et al. |
| 7,697,966 B2 | 4/2010 | Monfre et al. |
| 7,849,752 B2 | 12/2010 | Gregory et al. |
| 7,972,440 B2 * | 7/2011 | Houge ............... B24B 37/044 117/201 |
| 8,119,986 B1 | 2/2012 | Garvey, III et al. |
| 8,245,578 B2 | 8/2012 | Ranson et al. |
| 8,287,183 B2 * | 10/2012 | Shepard ............... F01D 5/186 374/43 |
| 8,307,715 B2 | 11/2012 | Ranson |
| 8,511,182 B2 | 8/2013 | Bjerge et al. |
| 8,600,147 B2 | 12/2013 | Iliopoulos et al. |
| 8,818,078 B2 | 8/2014 | Telfer et al. |
| 8,994,845 B2 | 3/2015 | Mankowski |
| 9,128,063 B2 | 9/2015 | Dooley |
| 9,200,889 B2 | 12/2015 | Swiergiel et al. |
| 9,291,527 B2 * | 3/2016 | Zoken ............... G01M 17/027 |
| 9,311,566 B2 | 4/2016 | Iliopoulos et al. |
| 9,316,571 B2 | 4/2016 | Müller et al. |
| 9,522,426 B2 * | 12/2016 | Das ............... B22F 3/1055 |
| 2011/0315897 A1 | 12/2011 | Romanovsky et al. |
| 2013/0013224 A1 | 6/2013 | Ito et al. |
| 2013/0194567 A1 | 8/2013 | Wan et al. |
| 2013/0202192 A1 | 8/2013 | Telfer et al. |
| 2014/0000380 A1 | 1/2014 | Slowik et al. |
| 2014/0267677 A1 | 9/2014 | Ward, Jr. et al. |
| 2015/0022357 A1 * | 1/2015 | Gettings ............... G01N 21/84 340/568.1 |
| 2015/0107368 A1 | 4/2015 | Harding et al. |
| 2015/0239043 A1 | 8/2015 | Shipper, Jr. et al. |
| 2016/0161242 A1 | 6/2016 | Cook et al. |
| 2016/0313114 A1 | 10/2016 | Tohme et al. |
| 2016/0354174 A1 | 12/2016 | Demir |

FOREIGN PATENT DOCUMENTS

| | | |
|---|---|---|
| WO | WO2011/163329 | 12/2011 |
| WO | WO2013/165495 | 11/2013 |
| WO | WO 2014/031957 | 2/2014 |

* cited by examiner

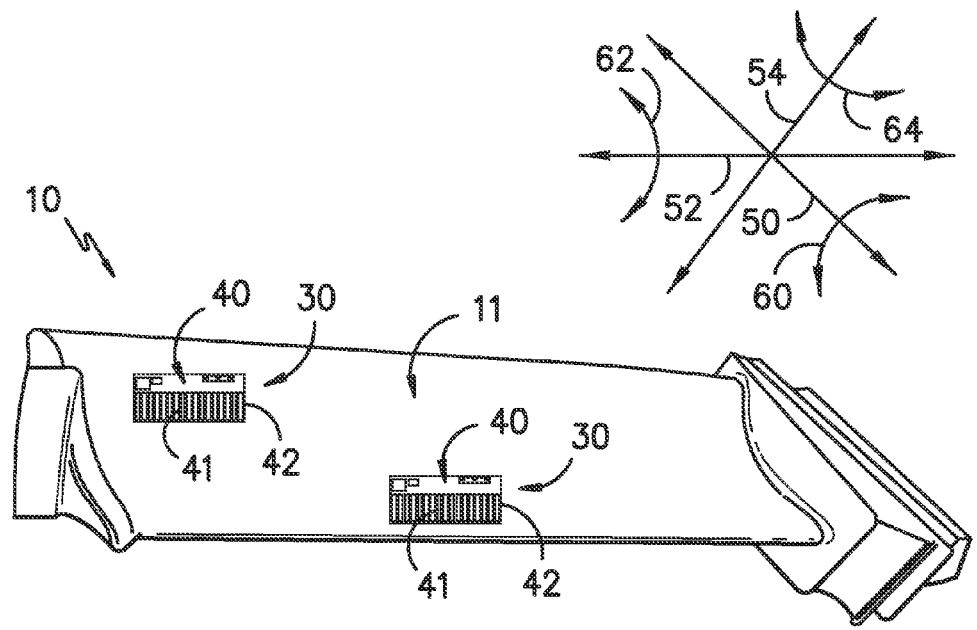
FIG. -1-
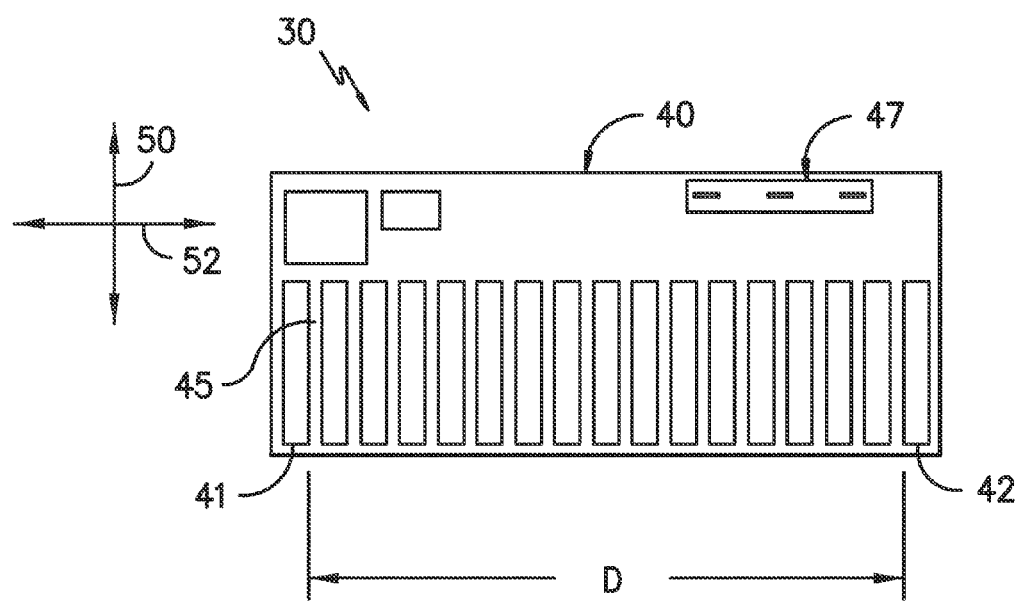
FIG. -2-

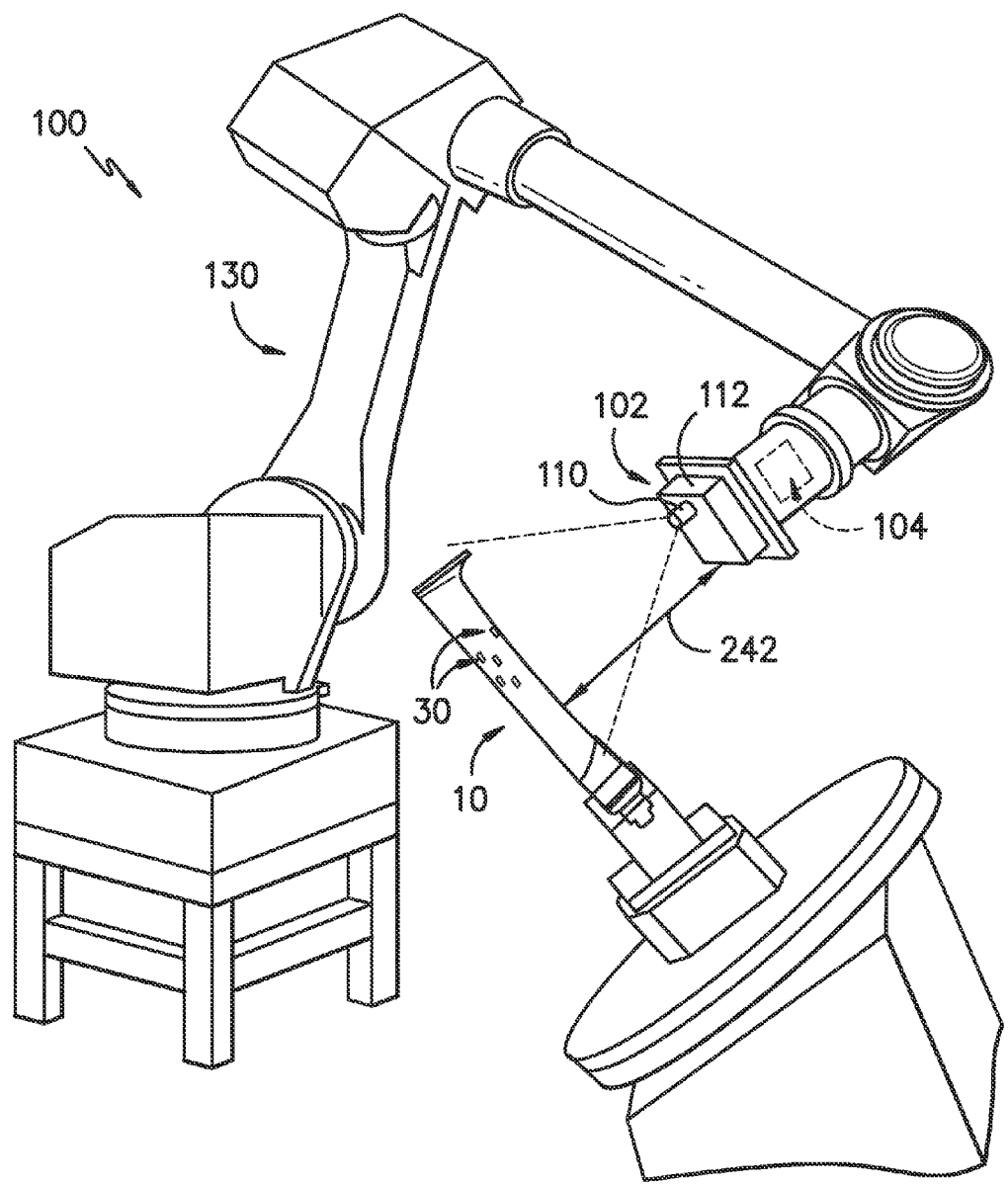
FIG. -3-

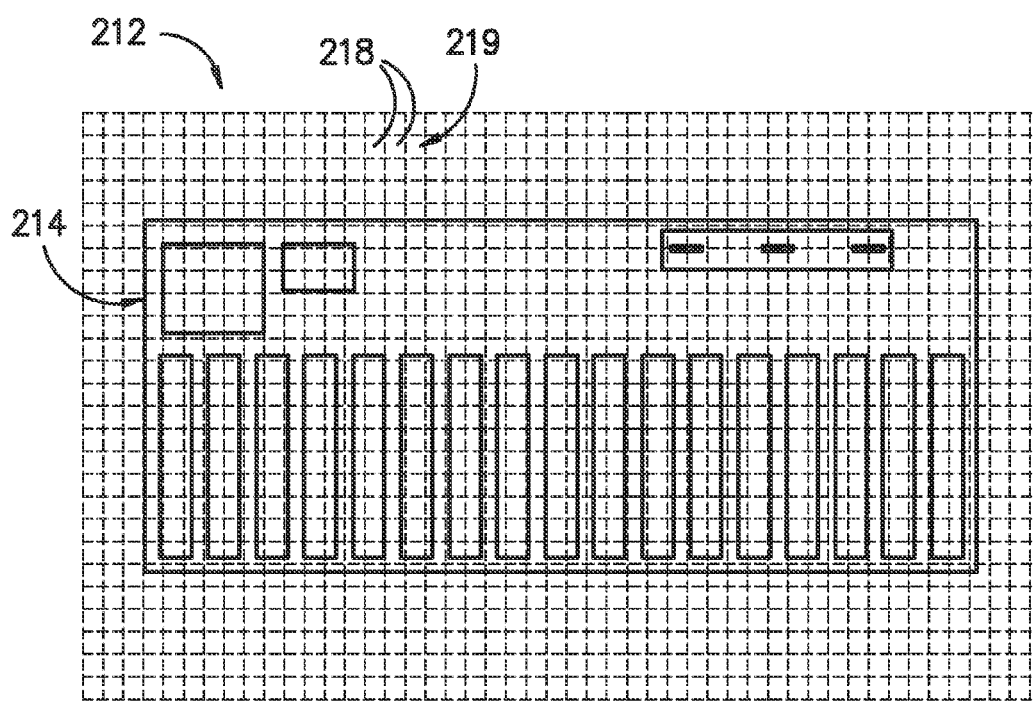
FIG. -4-

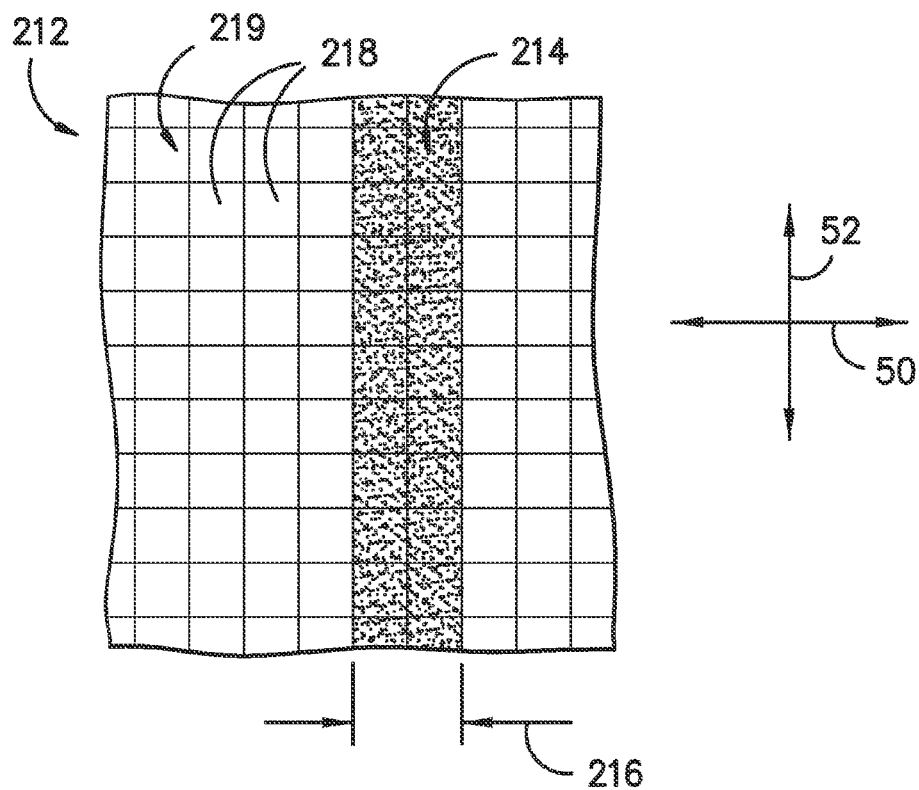
FIG. -5-
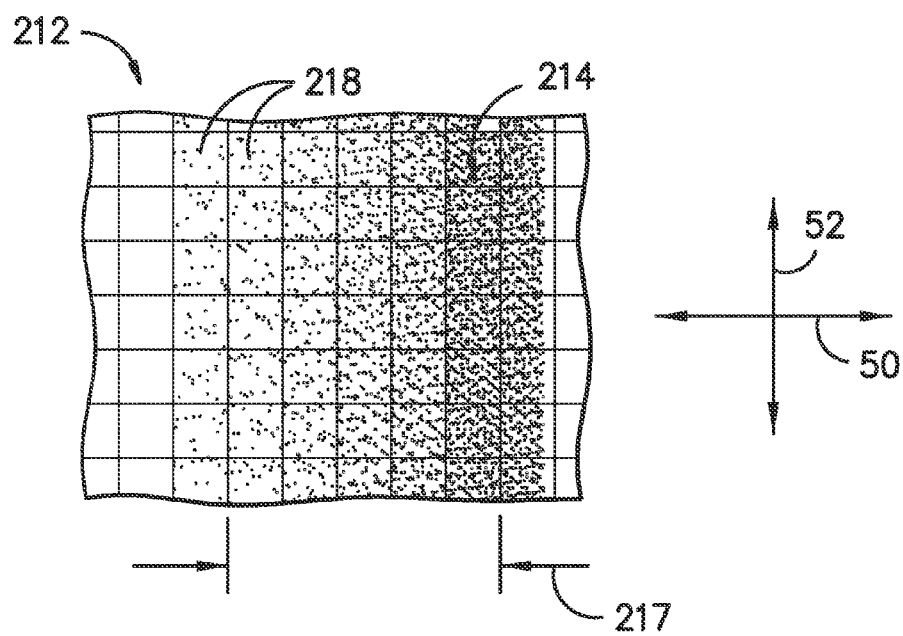
FIG. -6-

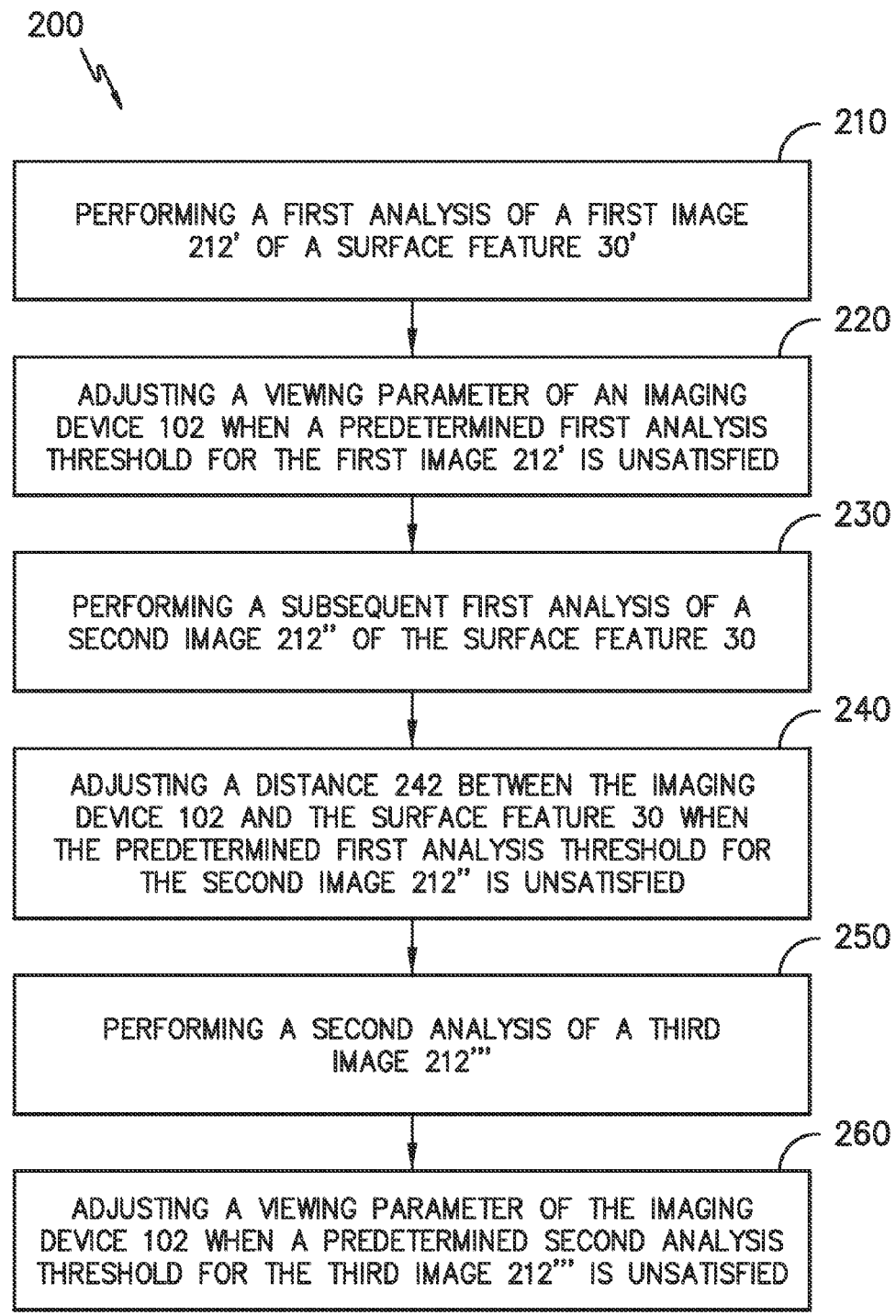
FIG. -7-

SYSTEMS AND METHODS FOR MONITORING COMPONENTS

FIELD OF THE INVENTION

The present disclosure relates generally systems and method for monitoring components, and more particularly to systems and methods which facilitate improved imaging of surface features configured on the components.

BACKGROUND OF THE INVENTION

Throughout various industrial applications, apparatus components are subjected to numerous extreme conditions (e.g., high temperatures, high pressures, large stress loads, etc.). Over time, an apparatus's individual components may suffer creep and/or deformation that may reduce the component's usable life. Such concerns might apply, for instance, to some turbomachines.

Turbomachines are widely utilized in fields such as power generation and aircraft engines. For example, a conventional gas turbine system includes a compressor section, a combustor section, and at least one turbine section. The compressor section is configured to compress air as the air flows through the compressor section. The air is then flowed from the compressor section to the combustor section, where it is mixed with fuel and combusted, generating a hot gas flow. The hot gas flow is provided to the turbine section, which utilizes the hot gas flow by extracting energy from it to power the compressor, an electrical generator, and other various loads.

During operation of a turbomachine, various components (collectively known as turbine components) within the turbomachine and particularly within the turbine section of the turbomachine, such as turbine blades, may be subject to creep due to high temperatures and stresses. For turbine blades, creep may cause portions of or the entire blade to elongate so that the blade tips contact a stationary structure, for example a turbine casing, and potentially cause unwanted vibrations and/or reduced performance during operation.

Accordingly, components may be monitored for creep. One approach to monitoring components for creep is to configure strain sensors on the components, and analyze the strain sensors at various intervals to monitor for deformations associated with creep strain.

One challenge in monitoring components and strain sensors thereon is obtaining images of the strain sensors that are of sufficient quality for subsequent deformation analyses to be accurate. Factors such as the illumination of the strain sensors, the surface properties of the component and the strain sensors, the viewing parameters for an image capture device being utilized to obtain the images (and potential misconfigurations thereof), and the relative positions of the image capture device and strain sensors can lead to images that are of insufficient quality. For example, the images can be blurred and/or out of focus. This can lead to inaccuracies in post-processing analyses of the images, such as for deformation analysis.

The need for improved imaging is not limited to stain sensor applications. Such need exists in other component applications. For example, improved imaging of cooling holes defined in the exterior surface of a component and/or other surface features configured on the exterior surface of a component is desired.

Accordingly, alternative systems and methods for monitoring components which facilitate improved imaging of surface features configured on the components are desired.

BRIEF DESCRIPTION OF THE INVENTION

Aspects and advantages of the invention will be set forth in part in the following description, or may be obvious from the description, or may be learned through practice of the invention.

In accordance with one embodiment of the present disclosure, a method for monitoring a component is disclosed. The component has an exterior surface. The method includes performing a first analysis of a first image of a surface feature configured on the exterior surface of the component, the first image obtained by an imaging device. The method further includes adjusting a viewing parameter of the imaging device when a predetermined first analysis threshold for the first image is unsatisfied, and performing a subsequent first analysis of a second image of the surface feature, the second image obtained by the imaging device. The method further includes adjusting a distance between the imaging device and the surface feature when the predetermined first analysis threshold for the second image is unsatisfied, and performing a second analysis of a third image, the third image obtained by the imaging device.

In accordance with another embodiment of the present disclosure, a system for monitoring a component is provided. The component has an exterior surface. The system includes an imaging device for obtaining images of a surface feature configured on the exterior surface of the component, and a processor in operable communication with the imaging device. The processor is configured for performing a first analysis of a first image of the surface feature, the first image obtained by the imaging device. The processor is further configured for adjusting a viewing parameter of the imaging device when a predetermined first analysis threshold for the first image is unsatisfied, and performing a subsequent first analysis of a second image of the surface feature, the second image obtained by the imaging device. The processor is further configured for adjusting a distance between the imaging device and the surface feature when the predetermined first analysis threshold for the second image is unsatisfied, and performing a second analysis of a third image, the third image obtained by the imaging device.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 is a perspective view of an exemplary component comprising a strain sensor in accordance with one or more embodiments of the present disclosure;

FIG. 2 is a top view of an exemplary strain sensor in accordance with one or more embodiments of the present disclosure;

FIG. 3 is a perspective view of a system for monitoring a component during locating of a surface feature in accordance with one or more embodiments of the present disclosure;

FIG. 4 is an image of a surface feature in accordance with one or more embodiments of the present disclosure;

FIG. 5 is an image of an edge of a surface feature utilized during a binary analysis of the image in accordance with one or more embodiments of the present disclosure;

FIG. 6 is an image of an edge of a surface feature utilized during a greyscale analysis of the image in accordance with one or more embodiments of the present disclosure; and FIG. 7 is a flow chart illustrating a method in accordance with one or more embodiments of the present disclosure.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Referring now to FIG. 1, a component 10 is illustrated with plurality of surface features 30, in this embodiment strain sensors 40, configured thereon. The component 10 (and more specifically the substrate of the overall component 10) can comprise a variety of types of components used in a variety of different applications, such as, for example, components utilized in high temperature applications (e.g., components comprising nickel or cobalt based superalloys). In some embodiments, the component 10 may comprise an industrial gas turbine or steam turbine component such as a combustion component or hot gas path component. In some embodiments, the component 10 may comprise a turbine blade, compressor blade, vane, nozzle, shroud, rotor, transition piece or casing. In other embodiments, the component 10 may comprise any other component of a turbine such as any other component for a gas turbine, steam turbine or the like. In some embodiments, the component may comprise a non-turbine component including, but not limited to, automotive components (e.g., cars, trucks, etc.), aerospace components (e.g., airplanes, helicopters, space shuttles, aluminum parts, etc.), locomotive or rail components (e.g., trains, train tracks, etc.), structural, infrastructure or civil engineering components (e.g., bridges, buildings, construction equipment, etc.), and/or power plant or chemical processing components (e.g., pipes used in high temperature applications).

The component 10 has an exterior surface 11 on or beneath which strain sensors 40 may be configured. Strain sensors 40 in accordance with the present disclosure may be configured on the exterior surface 11 using any suitable techniques, including deposition techniques; other suitable additive manufacturing techniques; subtractive techniques such as laser ablation, engraving, machining, etc.; appearance-change techniques such as annealing, direct surface discoloration, or techniques to cause local changes in reflectivity; mounting of previously formed strain sensors 40 using suitable mounting apparatus or techniques such as adhering, welding, brazing, etc.; or identifying pre-existing characteristics of the exterior surface 11 that can function as the components of a strain sensor 40. Additionally, in further alternative embodiments, strain sensors 40 can be configured beneath exterior surface 11 using suitable embedding techniques during or after manufacturing of the component 10.

Referring now to FIGS. 1 and 2, a strain sensor 40 generally comprises at least two reference points 41 and 42 that can be used to measure a distance D between said at least two reference points 41 and 42 at a plurality of time intervals. As should be appreciated to those skilled in the art, these measurements can help determine the amount of strain, strain rate, creep, fatigue, stress, etc. at that region of the component 10. The at least two reference points 41 and 42 can be disposed at a variety of distances and in a variety of locations depending on the specific component 10 so long as the distance D there between can be measured. Moreover, the at least two reference points 41 and 42 may comprise dots, lines, circles, boxes or any other geometrical or non-geometrical shape so long as they are consistently identifiable and may be used to measure the distance D there between.

The strain sensor 40 may comprise a variety of different configurations and cross-sections such as by incorporating a variety of differently shaped, sized, and positioned reference points 41 and 42. For example, as illustrated in FIG. 2, the strain sensor 40 may comprise a variety of different reference points comprising various shapes and sizes. Such embodiments may provide for a greater variety of distance measurements D such as between the outer most reference points (as illustrated), between two internal or external reference points, or any combination there between. The greater variety may further provide a more robust strain analysis on a particular portion of the component 10 by providing strain measurements across a greater variety of locations.

Furthermore, the values of various dimensions of the strain sensor 40 may depend on, for example, the component 10, the location of the strain sensor 40, the targeted precision of the measurement, application technique, and optical measurement technique. For example, in some embodiments, the strain sensor 40 may comprise a length and width ranging from less than 1 millimeter to greater than 300 millimeters. Moreover, the strain sensor 40 may comprise any thickness that is suitable for application and subsequent optical identification without significantly impacting the performance of the underlying component 10. Notably, this thickness may be a positive thickness away from the surface 11 (such as when additive techniques are utilized) or a negative thickness into the surface 11 (such as when subtractive techniques are utilized). For example, in some embodiments, the strain sensor 40 may comprise a thickness of less than from about 0.01 millimeters to greater than 1 millimeter. In some embodiments, the strain sensor 40 may have a substantially uniform thickness. Such embodiments may help facilitate more accurate measurements for subsequent strain calculations between the first and second reference points 41 and 42.

In some embodiments, the strain sensor 40 may comprise a positively applied square or rectangle wherein the first and second reference points 41 and 42 comprise two opposing sides of said square or rectangle. In other embodiments, the strain sensor 40 may comprise at least two applied reference points 41 and 42 separated by a negative space 45 (i.e., an area in which the strain sensor material is not applied). The negative space 45 may comprise, for example, an exposed portion of the exterior surface 11 of the component 10. Alternatively or additionally, the negative space 45 may comprise a subsequently applied visually contrasting material that is distinct from the material of the at least two reference points 41 and 42 (or vice versa).

As illustrated in FIG. 2, in some embodiments, the strain sensor 40 may include a unique identifier 47 (hereinafter "UID"). The UID 47 may comprise any type of barcode, label, tag, serial number, pattern or other identifying system that facilitates the identification of that particular strain sensor 40. In some embodiments, the UID 47 may additionally or alternatively comprise information about the component 10 or the overall assembly that the strain sensor 40 is configured on. The UID 47 may thereby assist in the identification and tracking of particular strain sensors 40, components 10 or even overall assemblies to help correlate measurements for past, present and future operational tracking.

The strain sensor 40 may thereby be configured in one or more of a variety of locations of various components 10. For example, as discussed above, the strain sensor 40 may be configured on a blade, vane, nozzle, shroud, rotor, transition piece or casing. In such embodiments, the strain sensor 40 may be configured in one or more locations known to experience various forces during unit operation such as on or proximate airfoils, platforms, tips or any other suitable location. Moreover, the strain sensor 40 may be configured in one or more locations known to experience elevated temperatures. For example, the strain sensor 40 may be configured on a hot gas path or combustion component 10.

As discussed herein and as shown in FIG. 1, multiple strain sensors 40 may be configured on a single component 10 or on multiple components 10. For example, a plurality of strain sensors 40 may be configured on a single component 10 (e.g., a blade) at various locations such that the strain may be determined at a greater number of locations about the individual component 10. Alternatively or additionally, a plurality of like components 10 (e.g., a plurality of blades) may each have a strain sensor 40 configured in a standard location so that the amount of strain experienced by each specific component 10 may be compared to other like components 10. In even some embodiments, multiple different components 10 of the same assembly (e.g., blades and vanes for the same turbomachine) may each have a strain sensor 40 configured thereon so that the amount of strain experienced at different locations within the overall assembly (i.e. turbomachine, etc.) may be determined.

It should be understood that the present disclosure is not limited to strain sensors 40 as illustrated herein. Rather, any suitable surface feature 30 configured on a component 10, such as on the exterior surface 11 thereof, is within the scope and spirit of the present disclosure. Examples of other suitable surface features 30 include cooling holes defined in the exterior surface, coating layers applied to the exterior surface 11 (wherein the exterior surface 11 is defined as that of a base component of the component 10), etc.

A coordinate system is additionally illustrated in FIGS. 1 and 2. The coordinate system includes an X-axis 50, a Y-axis 52, and a Z-axis 54, all of which are mutually orthogonal to each other. Additionally, a roll angle 60 (about the X-axis 50), a pitch angle 62 (about the Y-axis 52) and a yaw angle 64 (about the Z-axis 54) are illustrated.

Referring now to FIG. 3, a system 100 for monitoring a component 10 is illustrated. System 100 may include, for example, one or more surface features 30 which are configurable on the exterior surface 11 of one or more components 10 as discussed above. System 100 further includes an image capture device 102 and a processor 104. The image capture device 102 generally obtains images of the surface feature(s) 30, and the processor 104 generally analyzes the images and performs other functions as discussed herein. In particular, systems 100 in accordance with the present disclosure provide improved imaging by utilizing an iterative process that results in images of increased quality for post-processing. For example, resulting images that are utilized for post-processing may have sufficient sharpness for use in various types of post-processing. In one particular exemplary embodiments, the resulting images may be sufficient for use in deformation analysis, and may result in suitable accurate deformation analysis.

Imaging device 102 may include a lens assembly 110 and an image capture device 112, and may further include an illumination device, i.e. a light. Lens assembly 110 may generally magnify images viewed by the lens assembly 110 for processing by the image capture device 112. Lens assembly 110 in some embodiments may, for example, be a suitable camera lens, telescope lens, etc., and may include one or more lens spaced apart to provide the required magnification. Image capture device 112 may generally be in communication with the lens assembly 110 for receiving and processing light from the lens assembly 110 to generate images. In exemplary embodiments, for example, image capture device 112 may be a camera sensor which receives and processes light from a camera lens to generate images, such as digital images, as is generally understood. Imaging device 102 may further include a variety of settings, or viewing parameters, which may be applied and modified during operation thereof. The viewing parameters may affect the quality of the images obtained by the imaging device 102. In some embodiments, the viewing parameters may be setting that can be applied at various levels to the lens assembly 100 by the image capture device 112 or applied during processing of received light to obtain images by the image capture device 112. Viewing parameters may include, for example, aperture size, shutter speed, ISO setting, brightness setting, contrast setting, illumination level, etc. Each viewing parameter may be adjusted as required (and as discussed herein) to adjust the quality of an obtained image.

Image capture device 112 (and device 102 generally) may further be in communication with processor 104, via for example a suitable wired or wireless connection, for storing and analyzing the images from the image capture device 112 and device 102 generally. Notably, in exemplary embodiments processor 104 operates imaging devices 102 to perform various disclosed steps.

As discussed, system 100 may further include a processor 104. In general, as used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Processor 104 may also include various input/output channels for receiving inputs from and sending control signals to various other components with which the processor 104 is in communication, such as the imaging device 102, a robotic arm (discussed herein), etc. Processor 104 may generally perform various steps as discussed herein. Further, it should be understood that a processor 104 in accordance with the present disclosure may be a single master processor 104 in communication with the other various components of system 100, and/or may include a plurality of individual component processors, i.e. an imaging device processor, a data acquisition device processor, a robotic arm processor, etc. The various individual component processors may be in communication with each other and may further be in communication with a master processor, and these components may collectively be referred to as processor 104. Further, it should be noted that image capture device 112 may be a sub-component of processor 104, or may be a separate component from processor 104 which is in communication with processor 104.

As further illustrated in FIG. 3, system 100 may include a robotic arm 130. The robotic arm 130 may support and facilitate movement of other components system 100, such as the imaging device 102 and/or the processor 104. For example, the imaging device 102 may be mounted to the robotic arm 130. Processor 104 may be in communication with the robotic arm 130, such as with the various motors and/or drive components thereof, and may actuate the robotic arm 130 to move as required. Such movement may, in exemplary embodiments, position the imaging device 102 relative to the component 10 and surface feature(s) 30 thereon. In exemplary embodiments, the robotic arm 130 is a six-degree-of-freedom arm 130 which provides movement along axes 50, 52, 54 and along angles 60, 62, 64 (about the axes as discussed).

In alternative embodiments, system 100 may include other suitable devices for supporting and facilitating movement of other components system 100, such as the imaging device 102 and/or the processor 104. Such devices may, for example, be in communication with processor 104. For example, system 100 may include a boroscope, mobile robot (such as a snake robot), gantry system, or other suitable device. Some such devices may facilitate performance of various steps as discussed herein when the component 10 is in situ in an associated assembly, such as a turbomachine (i.e. a gas turbine 10). Alternatively, component 10 may be removed from the assembly when such steps are performed.

Referring now to FIG. 7, the present disclosure is further directed to methods 200 for monitoring components 10. Similar to systems 100, methods 200 may be utilized to obtain quality images of the surface features 30, such as for post-processing purposes. In exemplary embodiments, processor 104 may be utilized to perform various of the method steps 200 discussed herein. Accordingly, systems 100 and methods 200 may be configured for operation as discussed herein.

Method 200 may include, for example, the step 210 of performing a first analysis of a first image 212' of a surface feature 30. The first image 212' may be obtained by the imaging device 102, as discussed herein. FIG. 4 illustrates one embodiment of an image 212 of a surface feature 30, which may for example be obtained via imaging device 102 as discussed herein. Any suitable image analysis method which can evaluate the quality of the image 212' may be utilized when performing the first analysis. For example, a suitable pixel analysis which evaluates the sharpness of the image 212 based on comparisons of neighboring pixels of the image may be utilized. In accordance with one embodiment, the first analysis is a binary pixel analysis. This analysis is generally an analysis which differentiates a reference object (for example, the surface feature 30 or a portion thereof, such as an edge) from a background (for example, the component and background, respectively) on the basis of differences in color depth (i.e. differences in color or in greyscale). The analysis may be performed on each individual pixel 218 or groups of pixels 219 defining the image 212. For a binary analysis to occur, the number of bits-per-pixel of the image i.e. 128, 256, etc., is divided into two groups (generally a group which includes the lighter color depths and a group which includes the darker color depths). Each group is categorized as a reference object portion or a background portion. For example, the binary color depth analysis may categorize pixels or multi-pixel groups that are darker or lighter color depths as denoting a reference object (i.e. a surface feature or component thereof relative to a background), and may categorize pixels or multi-pixel groups that are the other of darker or lighter color depths as denoting a background.

As illustrated in FIG. 5, in exemplary embodiments, such binary analysis is performed on a component of the surface feature 30, such as an edge 214 thereof. For example a width 216 of the edge 214 may be measured during such analysis. Specifically, the number of pixels that are characterized in the group for the edge 214 (relative to a background) may be counted (such as along the X-axis 50 as shown or other width-wise axis). In general, a greater number of pixels in such group indicates a lower quality image 212'.

In accordance with another embodiment, the first analysis is a color scale or greyscale analysis on the bits-per-pixel of the image 212, i.e. 128, 256, etc. For example, in some embodiments, the first analysis is a 256 bit-per-pixel greyscale analysis. This analysis differentiates a reference object from a background on the basis of differences in color depth. Such analysis may be performed on each individual pixel 218 of an image 212, or on sub-sections of individual pixels. For example, pixels 218 may be divided into 100 sub-sections, 1000 sub-sections, 10,000 sub-sections, or any other suitable number of subsections, and the analysis may be performed on each individual sub-section. As discussed, a color scale or greyscale analysis is performed on the bits-per-pixel of the image i.e. 128, 256, etc. Accordingly, each pixel 218 or sub-section thereof is categorized as having a particular color depth per the 128, 256, etc. color depth scale.

As illustrated in FIG. 6, in exemplary embodiments, such color scale or greyscale analysis is performed on a component of the surface feature 30, such as an edge 214 thereof. For example a width 217 of the edge 214 may be measured during such analysis. Specifically, the number of pixels or sub-sections thereof that are included in a transition between a first color depth and a second, different color depth may be counted (such as along the X-axis 50 as shown or other width-wise axis). In general, a greater number of pixels in such transition indicates a lower quality image 212'.

Such analyses generally allow for the sharpness of the image 212 to be analyzed by, for example, analyzing the width in pixels 218 or sub-sections thereof of the surface feature 30 or various portions thereof. For example, it is generally desirable for the measured width 216, 217 to be low, thus indicating the relative sharpness of the image 212, and thus the quality of the image 212 for, for example, post-processing purposes.

Method 200 may further include, for example, the step 220 of adjusting one or more viewing parameters, as discussed herein, of the imaging device 102. Step 220 may occur, for example, when a predetermined first analysis threshold for the first image 212' is unsatisfied, thus indicating that the quality of the image 212 is below a predetermined quality threshold. For example, the predetermined first analysis threshold may be a first width threshold for the surface feature 30 or a component thereof, such as edge 214, of which a width 216 was measured. The first analysis threshold in these embodiments may be satisfied when the width 216 is below the first width threshold, and unsatisfied when the width 216 is above the first width threshold. Alternatively, the predetermined first analysis threshold may be a second width threshold for the surface feature 30 or a component thereof, such as edge 214, of which a width 217 was measured. The first analysis threshold in these embodiments may be satisfied when the width 217 is below the second width threshold, and unsatisfied when the width 217 is above the second width threshold. Adjustment of one or more viewing parameters may be performed when the predetermined first analysis threshold for the image 212 is unsatisfied, in an effort to obtain suitable levels for the viewing parameter(s) that result in images 212 of sufficient quality, as discussed herein.

In some embodiments, steps 210 and 220 may be repeated as desired to evaluate the quality of images 212 obtained by the imaging device 102. In some embodiments, the predetermined first analysis threshold for an image 212 may be satisfied. Post-processing may then, in some embodiments, occur using that image 212 and subsequent images with no further adjustment of the imaging device 102. Alternatively, after a certain (in some embodiments predetermined) number of iterations of steps 210 and 220, additional evaluation and adjustment may occur.

For example, method 200 may further include, for example, the step 230 of performing a subsequent first analysis (as discussed herein) of a second image 212" of the surface feature 30. The second image 212" image may, for example, be obtained by the imaging device 202 as discussed herein. Method 200 may further include, for example, the step 240 of adjusting a distance 242 (for example along the Z-axis 54) (see, e.g., FIG. 3) between the imaging device 102 and the surface feature 30 when the predetermined first analysis threshold (as discussed herein) for the second image 212" is unsatisfied. For example, arm 130 or another suitable device of system 100 may move the imaging device 102 (such as the lens assembly 110) thereof relative to the surface feature 30 to adjust distance 242.

Further, method 200 may include, for example, the step 250 of performing a second analysis of a third image 212'''. The third image 212''' may, for example, be obtained by the imaging device 102, and may be obtained after step 240 (and/or 220). In exemplary embodiments, the first and second analyses may be different. Alternatively, the first and second analyses may be the same. In some embodiments, the second analysis may be a binary pixel analysis, as discussed herein, while in alternative embodiments, the second analysis may be a color scale or grey scale analysis, as discussed herein.

Method 200 may further include, for example, the step 260 of adjusting a viewing parameter of the imaging device 102, as discussed herein. Such step may occur, for example, when a predetermined second analysis threshold for the first image 212''' is unsatisfied, thus indicating that the quality of the image 212 is below a predetermined quality threshold. For example, the predetermined second analysis threshold may be a first width threshold for the surface feature 30 or a component thereof, such as edge 214, of which a width 216 was measured. The second analysis threshold in these embodiments may be satisfied when the width 216 is below the first width threshold, and unsatisfied when the width 216 is above the first width threshold. Alternatively, the predetermined second analysis threshold may be a second width threshold for the surface feature 30 or a component thereof, such as edge 214, of which a width 217 was measured. The second analysis threshold in these embodiments may be satisfied when the width 217 is below the second width threshold, and unsatisfied when the width 217 is above the second width threshold. Adjustment of one or more viewing parameters may be performed when the predetermined second analysis threshold for the image 212 is unsatisfied, in an effort to obtain suitable levels for the viewing parameter(s) that result in images 212 of sufficient quality, as discussed herein.

Notably, in some embodiments, the predetermined first analysis threshold and the predetermined second analysis threshold may be different. Alternatively, the predetermined first analysis threshold and the predetermined second analysis threshold may be same.

Additional adjustments of the viewing parameters and/or the distance 242 may be performed as necessarily in accordance with the present disclosure, such as until one of both of the predetermined first and second analysis thresholds are satisfied. When satisfied, the images 212 are deemed to be of sufficient quality for post-processing, as discussed herein. Notably, in exemplary embodiments, various steps 210, 220, 230, 240, 250 and/or 260 as discussed herein may be performed automatically. Accordingly, no user input may be required (i.e. between steps) for such steps to be performed. For example, processor 104 may perform such steps automatically in order to obtain images 212 of sufficient quality for post processing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for monitoring a component, the component having an exterior surface, the method comprising:
   performing a first analysis of a first image of a surface feature configured on the exterior surface of the component, the first image obtained by an imaging device;
   adjusting a viewing parameter of the imaging device when a predetermined first analysis threshold for the first image is unsatisfied;
   performing a subsequent first analysis of a second image of the surface feature, the second image obtained by the imaging device;
   adjusting a distance between the imaging device and the surface feature when the predetermined first analysis threshold for the second image is unsatisfied; and
   performing a second analysis of a third image of the surface feature, the third image obtained by the imaging device.

2. The method of claim 1, wherein the first analysis is different from the second analysis.

3. The method of claim 1, wherein the first analysis is a binary pixel analysis.

4. The method of claim 1, wherein the second analysis is a greyscale pixel analysis.

5. The method of claim 4, wherein the second analysis is a 256 bit-per-pixel greyscale analysis.

6. The method of claim 4, further comprising adjusting a viewing parameter of the imaging device when a predetermined second analysis threshold for the third image is unsatisfied.

7. The method of claim 1, wherein the step of adjusting the viewing parameter is performed automatically when the predetermined first analysis threshold for the second image is unsatisfied, and wherein the step of adjusting the distance is performed automatically when the predetermined first analysis threshold for the second image is unsatisfied.

8. The method of claim 1, wherein the surface feature is a strain sensor and the component is a turbine component.

9. A system for monitoring a component, the component having an exterior surface, the system comprising:
an imaging device for obtaining images of a surface feature configured on the exterior surface of the component; and
a processor in operable communication with the imaging device, the processor configured for:
performing a first analysis of a first image of the surface feature, the first image obtained by the imaging device;
adjusting a viewing parameter of the imaging device when a predetermined first analysis threshold for the first image is unsatisfied;
performing a subsequent first analysis of a second image of the surface feature, the second image obtained by the imaging device;
adjusting a distance between the imaging device and the surface feature when the predetermined first analysis threshold for the second image is unsatisfied; and
performing a second analysis of a third image of the surface feature, the third image obtained by the imaging device.

10. The system of claim 9, wherein the first analysis is different from the second analysis.

11. The system of claim 9, wherein the first analysis is a binary pixel analysis.

12. The system of claim 9, wherein the second analysis is a greyscale pixel analysis.

13. The system of claim 12, wherein the second analysis is a 256 bit-per-pixel greyscale analysis.

14. The system of claim 12, wherein the processor is further configured for adjusting a viewing parameter of the imaging device when a predetermined second analysis threshold for the third image is unsatisfied.

15. The system of claim 9, wherein the step of adjusting the viewing parameter is performed automatically when the predetermined first analysis threshold for the second image is unsatisfied, and wherein the step of adjusting the distance is performed automatically when the predetermined first analysis threshold for the second image is unsatisfied.

16. The system of claim 9, wherein the surface feature is a strain sensor and the component is a turbine component.

17. A method for monitoring a component, the component having an exterior surface, the method comprising:
performing a first analysis of a first image of a surface feature configured on the exterior surface of the component, the first image obtained by an imaging device, wherein the first analysis is a binary pixel analysis;
adjusting a viewing parameter of the imaging device when a predetermined first analysis threshold for the first image is unsatisfied, wherein the predetermined first analysis threshold is a first width threshold for an edge of the surface feature;
performing a subsequent first analysis of a second image of the surface feature, the second image obtained by the imaging device;
adjusting a distance between the imaging device and the surface feature when the predetermined first analysis threshold for the second image is unsatisfied; and
performing a second analysis of a third image of the surface feature, the third image obtained by the imaging device.

18. The method of claim 17, wherein the first analysis is different from the second analysis.

19. The method of claim 17, wherein the second analysis is a greyscale pixel analysis.

20. The method of claim 17, wherein the step of adjusting the viewing parameter is performed automatically when the predetermined first analysis threshold for the second image is unsatisfied, and wherein the step of adjusting the distance is performed automatically when the predetermined first analysis threshold for the second image is unsatisfied.

21. A system for monitoring a component, the component having an exterior surface, the system comprising:
an imaging device for obtaining images of a surface feature configured on the exterior surface of the component; and
a processor in operable communication with the imaging device, the processor configured for:
performing a first analysis of a first image of the surface feature, the first image obtained by the imaging device, wherein the first analysis is a binary pixel analysis;
adjusting a viewing parameter of the imaging device when a predetermined first analysis threshold for the first image is unsatisfied, wherein the predetermined first analysis threshold is a first width threshold for an edge of the surface feature;
performing a subsequent first analysis of a second image of the surface feature, the second image obtained by the imaging device;
adjusting a distance between the imaging device and the surface feature when the predetermined first analysis threshold for the second image is unsatisfied; and
performing a second analysis of a third image of the surface feature, the third image obtained by the imaging device.

22. The system of claim 21, wherein the first analysis is different from the second analysis.

23. The system of claim 21, wherein the second analysis is a greyscale pixel analysis.

24. The system of claim 21, wherein the step of adjusting the viewing parameter is performed automatically when the predetermined first analysis threshold for the second image is unsatisfied, and wherein the step of adjusting the distance is performed automatically when the predetermined first analysis threshold for the second image is unsatisfied.

25. A method for monitoring a component, the component having an exterior surface, the method comprising:
performing a first analysis of a first image of a surface feature configured on the exterior surface of the component, the first image obtained by an imaging device;
adjusting a viewing parameter of the imaging device when a predetermined first analysis threshold for the first image is unsatisfied;
performing a subsequent first analysis of a second image of the surface feature, the second image obtained by the imaging device;
adjusting a distance between the imaging device and the surface feature when the predetermined first analysis threshold for the second image is unsatisfied;
performing a second analysis of a third image of the surface feature, the third image obtained by the imaging device, wherein the second analysis is a 256 bit-per-pixel greyscale pixel analysis; and adjusting a viewing parameter of the imaging device when a predetermined second analysis threshold for the third image is unsatisfied, wherein the predetermined second analysis threshold is a second width threshold for an edge of the surface feature.

26. The system of claim 25, wherein the first analysis is different from the second analysis.

27. A system for monitoring a component, the component having an exterior surface, the system comprising:
   an imaging device for obtaining images of a surface feature configured on the exterior surface of the component; and
   a processor in operable communication with the imaging device, the processor configured for:
      performing a first analysis of a first image of the surface feature, the first image obtained by the imaging device;
      adjusting a viewing parameter of the imaging device when a predetermined first analysis threshold for the first image is unsatisfied;
      performing a subsequent first analysis of a second image of the surface feature, the second image obtained by the imaging device;
      adjusting a distance between the imaging device and the surface feature when the predetermined first analysis threshold for the second image is unsatisfied;
      performing a second analysis of a third image of the surface feature, the third image obtained by the imaging device, wherein the second analysis is a 256 bit-per-pixel greyscale pixel analysis;
      adjusting a viewing parameter of the imaging device when a predetermined second analysis threshold for the third image is unsatisfied, wherein the predetermined second analysis threshold is a second width threshold for an edge of the surface feature.

28. The system of claim 27, wherein the first analysis is different from the second analysis.

* * * * *